US006752327B2

(12) United States Patent
Martens, III et al.

(10) Patent No.: US 6,752,327 B2
(45) Date of Patent: Jun. 22, 2004

(54) ATOMIZER WITH TILTED ORIFICE PLATE AND REPLACEMENT RESERVOIR FOR SAME

(75) Inventors: Edward J. Martens, III, Racine, WI (US); Thomas A. Helf, New Berlin, WI (US); David A. Tomkins, Racione, WI (US)

(73) Assignee: S. C. Johnson & Son, Inc., Racine, WI (US)

(*) Notice: Subject to any disclaimer, the term of this patent is extended or adjusted under 35 U.S.C. 154(b) by 44 days.

(21) Appl. No.: 10/271,841

(22) Filed: Oct. 16, 2002

(65) Prior Publication Data

US 2004/0074984 A1 Apr. 22, 2004

(51) Int. Cl.[7] .................................................. B05B 1/08
(52) U.S. Cl. .................................... 239/102.2; 239/596
(58) Field of Search .......................... 239/102.1, 102.2, 239/145, 504, 509, 513, 522, 596

(56) References Cited

U.S. PATENT DOCUMENTS 3,970,250 A * 7/1976 Drews ..................... 239/102.2
4,294,407 A 10/1981 Reichl et al. ............... 239/102
4,301,093 A 11/1981 Eck ............................... 261/1
4,479,609 A 10/1984 Maeda et al. ............... 239/102
4,537,354 A * 8/1985 Eith ........................ 239/102.2
4,790,479 A 12/1988 Matsumoto et al. ........ 239/102
4,793,339 A 12/1988 Matsumoto et al. ........ 128/200
5,297,734 A 3/1994 Toda .......................... 239/102
5,299,739 A 4/1994 Takahashi et al. .......... 239/102
5,518,179 A 5/1996 Humberstone et al. ..... 239/102
5,657,926 A 8/1997 Toda .......................... 239/102
5,996,903 A 12/1999 Asai et al. .................. 239/102
6,030,558 A 2/2000 Smith et al. .................. 264/41
6,143,370 A * 11/2000 Panagiotou et al. ........ 427/422
6,293,474 B1 * 9/2001 Helf et al. ............... 239/102.2
6,296,196 B1 10/2001 Denen et al. .................. 239/4
6,341,732 B1 * 1/2002 Martin et al. .................. 239/4
6,378,780 B1 * 4/2002 Martens, III et al. .... 239/102.2
6,382,522 B2 * 5/2002 Tomkins et al. ......... 239/102.2
6,386,462 B1 * 5/2002 Martens, III ................... 239/4
6,439,474 B2 * 8/2002 Denen ..................... 239/102.2
6,446,880 B1 * 9/2002 Schram et al. .............. 239/145
2003/0102384 A1 * 6/2003 Walter et al. ........... 239/102.2

FOREIGN PATENT DOCUMENTS

JP 359052561 A * 3/1984

* cited by examiner

*Primary Examiner*—William E. Tapolcai
*Assistant Examiner*—Mohammad M Ali

(57) ABSTRACT

A vibratory plate liquid atomization device (10) having a tilted orifice plate (34) which is vibrated by a piezoelectric actuator (36); and a novel replaceable liquid reservoir (40) having a vertically extending, dimensionally stable, liquid delivery system (44) with a non-horizontal upper surface (**44*a***).

16 Claims, 4 Drawing Sheets

ATOMIZER WITH TILTED ORIFICE PLATE AND REPLACEMENT RESERVOIR FOR SAME

BACKGROUND OF THE INVENTION

1. Field of the Invention

This invention relates to replaceable liquid reservoirs and more particularly to reservoirs which are provided with capillary type liquid delivery systems for delivering liquid from within a reservoir to a vibrating atomizer plate located above the reservoir.

2. Description of the Related Art

U.S. Pat. Nos. 4,301,093 and 5,657,926 show vibrating plate atomizers in which a reservoir is held beneath a piezoelectrically driven vibratory atomization plate. A capillary type liquid delivery system, comprising a fabric wick, extends up from within the reservoir to a location under the vibrating atomization plate to deliver liquid from within the reservoir to the underside of the plate to be atomized thereby.

U.S. Pat. No. 5,518,179 also shows a vibratory type atomizer in which liquid from a fluid source is delivered by a foam capillary material which is lightly compressed against a vibratory perforate membrane. The perforate membrane is shown to be located in a vertical plane; and the foam capillary material is shown to extend upwardly from the fluid source and to be bent through 90° so that its upper end rests flat against the face of the perforate membrane.

Other atomizing devices which atomize liquids from a reservoir by means of a vibrating plate and which use a liquid delivery system to transfer the liquid from the reservoir to the plate are shown in U.S. Pat. Nos. 4,294,407, 4,479,609, 4,790,479, 4,793,339, 5,297,734, 5,299,739 and 5,996,903.

It is often necessary or desirable to orient the vibratory orifice plate of an atomizer device so that it ejects atomized or aerosolized liquid droplets at an angle to the vertical. For example, where the atomization device is to be mounted on a wall, the ejected liquid droplets should be directed away from the wall so that they do not collect and do damage to the wall surface. This problem can be overcome by orienting the vibratory perforate membrane or orifice plate so that its plane is tilted from the horizontal and away from nearby walls or other vertical surfaces.

A problem occurs when liquid is to be transferred by capillary action from a reservoir to a vibrating perforate membrane or vibrating orifice plate which does not extend in a horizontal plane. In the past, the liquid delivery systems of vibratory type atomization devices, which usually comprised a fabric wick or a solid capillary element, exited from the reservoir in a vertical direction and then became bent at a location above the reservoir so that the upper end of the capillary element terminated flat against the surface of the perforate membrane or orifice plate. As a result, there was a tendency for liquid to drip from the capillary element and accumulate outside the reservoir without being atomized or recoverable. Also where the liquid is aggressive, for example in the case of many liquid fragrances or insecticides, such leakage of the liquid can damage the surfaces on which it accumulates.

SUMMARY OF THE INVENTION

According to one aspect of the invention there is provided a novel atomizer for ejecting small liquid droplets into the atmosphere. This novel atomizer comprises a housing, a vibratory orifice plate which extends in a plane and which is mounted in the housing with its plane tilted from the horizontal. The orifice plate has a plurality of small orifices formed in its center region. A vibratory actuator is coupled to the orifice plate for causing it to vibrate rapidly in a direction perpendicular to its plane.

A replaceable liquid reservoir is removably mounted within the housing below the orifice plate. The reservoir comprises a liquid container for containing a supply of liquid to be atomized; and it further comprises a solid, porous and dimensionally stable elongated liquid delivery member. The liquid delivery member extends up along a vertical axis from a location within and near the bottom of the liquid container and through an upper opening in the container to a location above the container. The liquid delivery member has an upper end which is located above the container and which forms an upper liquid delivery surface. The liquid delivery surface itself is tilted from the horizontal and it is positioned in the housing such that it lies along the plane of the orifice plate. As a result, maximum area of contact and maximum effectiveness of liquid transfer is achieved between the liquid delivery surface and the orifice plate. The liquid delivery surface at the upper end of the liquid delivery member is also contained within and does not extend beyond the extent of the horizontal cross-section of the liquid delivery member. Consequently any excess liquid which comes off the edge of the liquid delivery surface, merely runs back along a vertical side surface of the liquid delivery member and back into the liquid container without dripping onto nearby surfaces outside the container.

According to another aspect of the invention, there is provided a novel replaceable liquid reservoir for use with a vibrating orifice plate atomizer device. This novel reservoir comprises a liquid container for containing a supply of liquid to be atomized and a solid, porous and elongated, dimensionally stable, liquid delivery member which extends along a vertical axis from within the liquid container and out through an upper opening of the container to a location along the vertical axis above the liquid container. The liquid delivery member is formed with an upper end which is located along the vertical axis and above the container. The upper end of the liquid delivery member is formed as a liquid delivery surface which intersects and forms an acute angle with the vertical axis. Thus the liquid delivery surface can lay flat against a tilted orifice plate within an atomizer device to provide maximum effectiveness of liquid transfer to the tilted orifice plate. Further, the liquid delivery surface is contained within and does not extend beyond the edge of a horizontal cross-section of the liquid delivery member. Consequently excess liquid which flows from the edge of the liquid delivery surface, merely runs back along a vertical side surface of the liquid delivery member and back into the liquid container without dripping onto nearby surfaces outside the container.

DETAILED DESCRIPTION OF THE PREFERRED EMBODIMENTS

Figure 1:
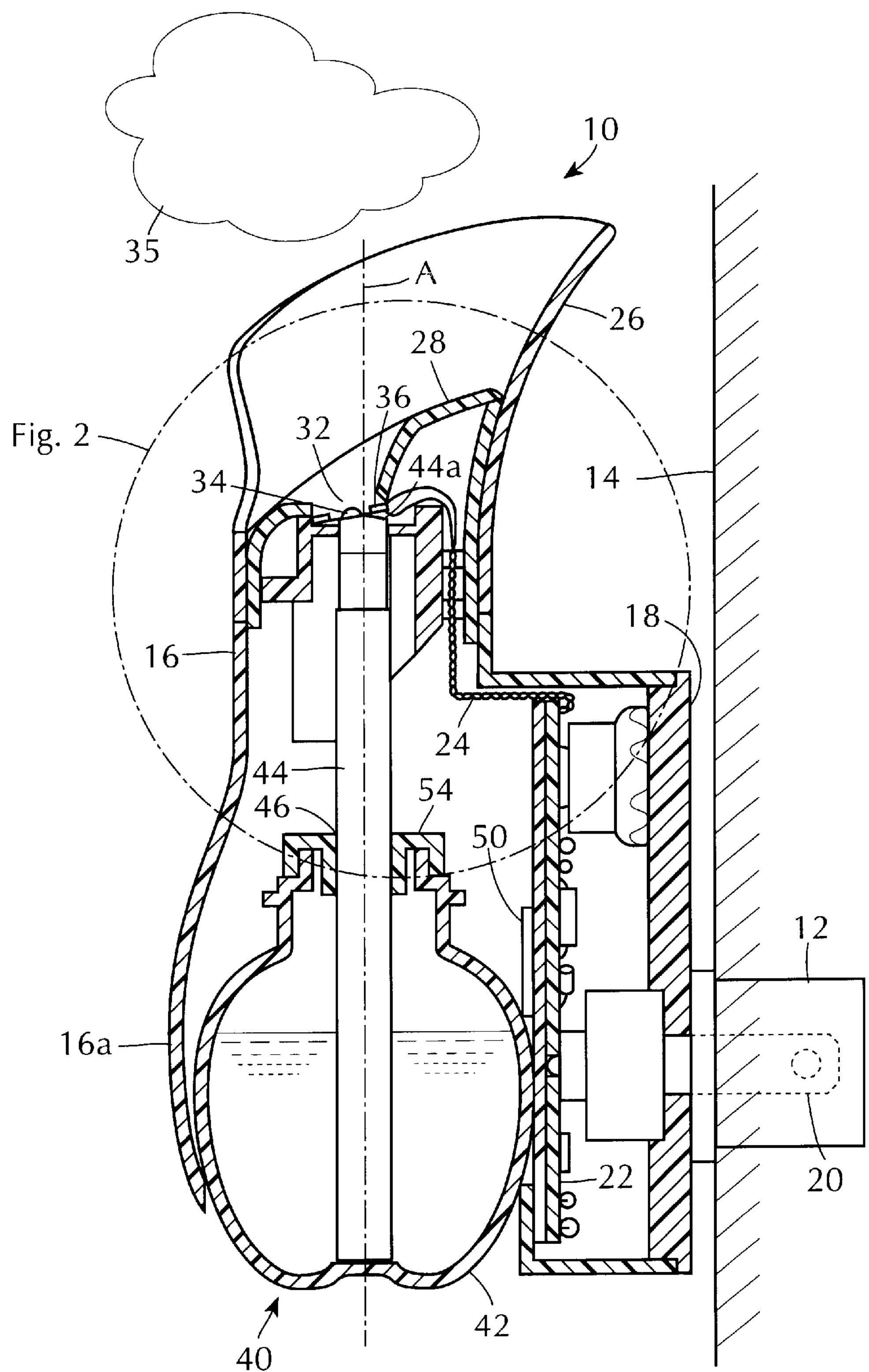
FIG. 1 is a side elevational section view of an atomizer according to the invention.

As shown in FIG. 1, an atomizer device 10 according to the present invention is plugged into an electrical outlet 12 in a wall 14. The atomizer device comprises a hollow outer housing 16 which has a flat mounting surface 18 from which electrical prongs 20 extend. These prongs can be plugged into the outlet 12 thereby to support the atomizer device 10 and, at the same time, to provide it with electrical power.

The electrical prongs 20 are connected inside the housing 16 to electrical circuits formed on a printed circuit board 22. The circuits on the printed circuit board 22, which may be as described in copending application Ser. No. 10/005,655, filed on Dec. 3, 2001, produce alternating electrical voltages on a pair of wires 24. The frequency and amplitude of these alternating voltages is controlled by the circuits on the printed circuit board 22. In cases where the atomizer device is battery driven, the manner in which these alternating voltages are generated may also be as described in U.S. Pat. No. 6,296,196.

Figure 2:
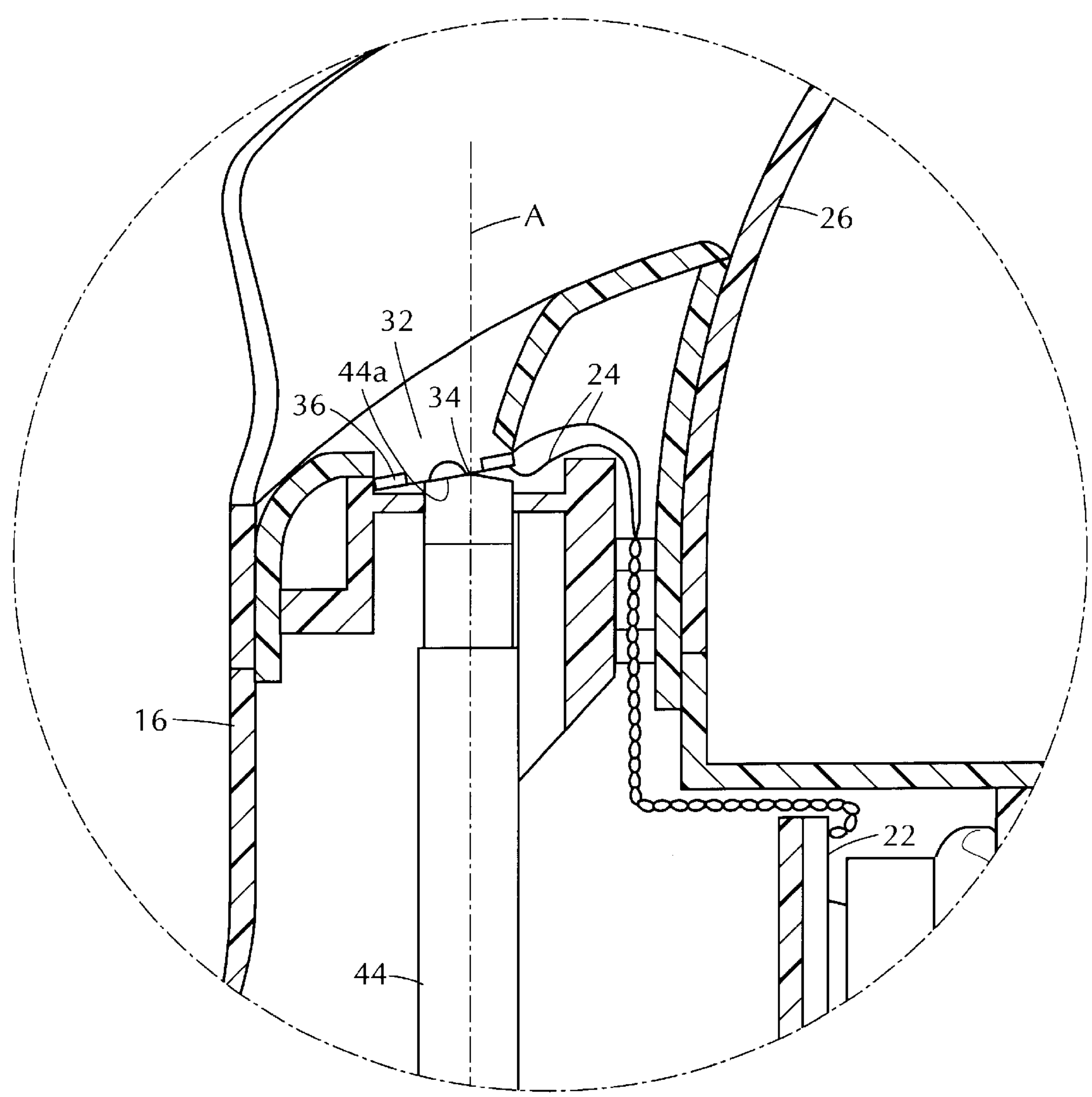
FIG. 2 is an enlarged fragmentary view of a portion of the atomizer device indicated by a phantom line 2 in FIG. 1.

The region of the housing 16 behind the mounting surface 18 is formed as a flared chimney 26. A slanted wall 28 extends across the interior of the chimney 26 and the wall 28 is formed with an ejection opening 32. As best shown in FIG. 2, an atomization assembly comprising a vibratory orifice plate 34 and an annularly shaped piezoelectric actuator 36 are arranged just under, and in alignment with, the ejection opening 32.

The wires 24 connect the opposite sides of the actuator 36 with circuits mounted on the printed circuit board 22. In this manner alternating voltages produced by these circuits impose alternating electrical fields across the piezoelectric actuator and cause the actuator to expand and contract in radial directions. The orifice plate 34 extends across and is affixed to the actuator 36, either directly or through an intermediate element, in a manner such that the radial expansion and contraction of the actuator is communicated to the orifice plate and causes it to vibrate up and down in a direction perpendicular to its plane. The orifice plate 34 is provided in its center region with a plurality of small orifices which extend through the plate. Upon vibration of the plate, liquid which is supplied to the underside of the plate is broken up into small droplets and ejected upwardly from the upper surface of the plate and out through the ejection opening 32 in the form of a puff or cloud 35.

It will be noted that the orifice plate 34, as well as the actuator 36 are tilted from the horizontal in a direction away from the wall 14. This tilt allows the atomized liquid to be ejected in a direction away form the wall 14 so that it does not impinge on the wall and damage it by chemical attack, etc.

Liquid is supplied to the orifice plate 34 from a replaceable liquid reservoir assembly 40 which comprises a liquid container 42 and a solid, porous and dimensionally stable liquid delivery system in the form of a solid capillary element 44. The capillary element extends upwardly along a vertical axis A from within the container 42 and passes through an opening 46 in the top thereof to a fixed location adjacent the underside of the orifice plate 34. A liquid to be atomized, which is contained within the liquid container 42, is drawn up out of the container by capillary action in the capillary element 44 and supplied to the underside of the orifice plate 34. The capillary element 44 is a solid, porous and dimensionally stable rod-like member. That is, the element 44 contains minute interconnected open cells which form capillary passages to draw liquid up from the liquid container 42 toward the upper end of the element 44.

In order to ensure that liquid will be delivered adequately and evenly to the underside of the orifice plate 34, the capillary element 44 is formed with an upper surface **44*a* which is tapered at the same angle from the vertical axis A as the tilt of the orifice plate. Thus the upper surface 44*a* lies against the plate and provides maximum contact with the plate. This tilt may be, for example, about 80° with respect to the axis A; however the exact amount of the tilt is not critical to this invention, so long as it changes the direction along which the puff or cloud 35** of atomized particles is ejected, from vertical to a direction other than vertical.

It should be noted that the entire upper surface **44*a* of the capillary element 44 is contained within the cross-sectional area of the element. Thus the capillary element 44 need not be curved or bent to provide flat contact of its upper end with the plate 34. Because of this there is no danger that liquid which does not become ejected by the orifice plate 34 will drip onto surrounding regions of the atomizer assembly. At most, the excess liquid will run down the sides of the capillary element 44 and back into the container 42**.

As can be seen in FIG. 1, the reservoir assembly 40, including both the liquid container 42 and the capillary element 44 is removable as a unit from the atomizer device 10 so that it may be replaced with another reservoir assembly, for example when the liquid needs to be replenished or when it is desired to atomize a different liquid. As shown in FIG. 1 a lower portion **16*a* of the housing 16 is resiliently bendable to hold the liquid container 42 against an opposite inner wall 48 in the housing. The inner wall 48 is formed with a shoulder or other indentation 50 which locates the liquid container 42 in a specific predetermined position within the housing 16; and it is held in place by the resiliently bendable lower portion 16*a*. When it is desired to remove and replace the reservoir assembly 40, it is only necessary to pull down on the liquid container 42 so as to cause the lower portion 16*a* of the housing 16 to bend outwardly and allow the reservoir assembly 40 to be pulled down and out from the atomizer device. A new reservoir assembly can then simply be inserted in the housing 16** and pushed into place so as to be held in a precise location within the atomizer device.

Figure 3:
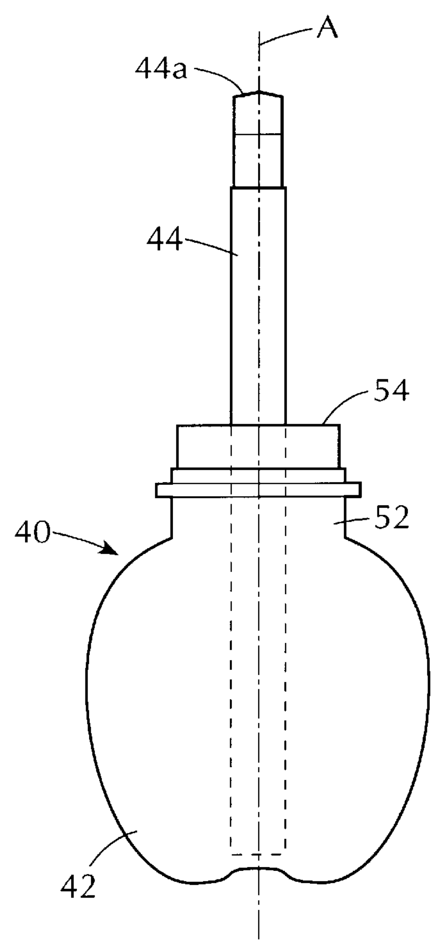
FIGS. 3 and 4 are side and front elevational views, respectively, of a novel replacement reservoir according to the invention.
Figure 4:
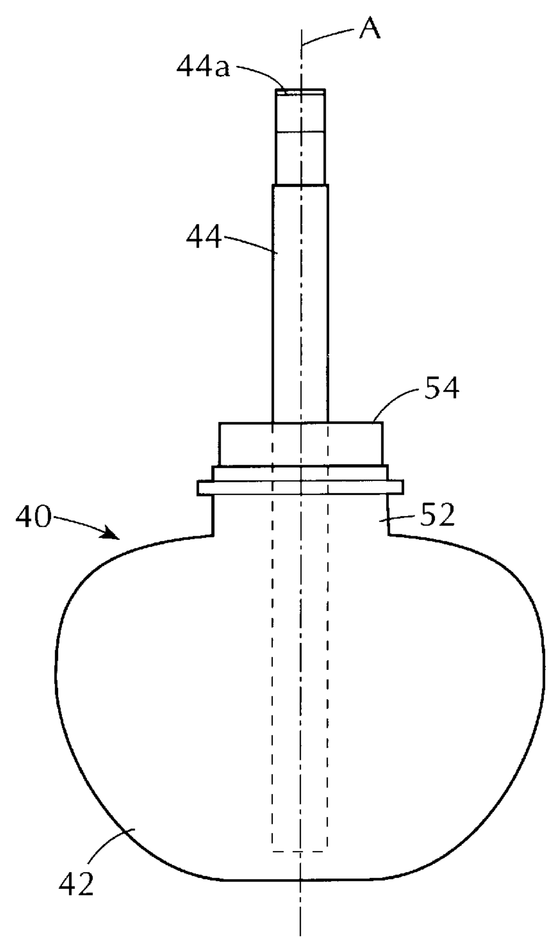

FIG. 3 shows the reservoir assembly 40, which is a self contained unit, removed from the atomizer device. As can be seen, the liquid container 42 is formed with an open upper neck 52 which is closed by a plug 54. The plug 54 is open at its center; and the capillary element 44 extends in a vertical direction from the bottom of the interior of the liquid container 42 and out through the center of the plug 54 to a predetermined location above the liquid container. Because the capillary element 44 has a dimensionally stable construction (as opposed to that of a fibrous wick), its tapered upper surface **44*a* is thereby maintained at a precise location above the liquid container 42. This allows the surface 44*a*** to be positioned so that it lays against the underside of the orifice plate in the atomizer device without pressing too hard on it, thereby providing maximum effectiveness in the transfer of liquid from the capillary element to the orifice plate.

The capillary element 44 may be formed by bringing together small particles of a thermoplastic polymer and subjecting them to a temperature and pressure at which the molecules at the surface of each small particle become mobile enough to mechanically intermingle with the molecules at the surface of any adjoining pellets, thus forming a bond between them. The small particles are maintained at a proper temperature and temperature until a desired degree of bonding has occurred After an appropriate amount of time, the mass of small particles is cooled to room temperature. The result is a porous structure molded into a specific product shape. A suitable process for forming the capillary element 44 is described in U.S. Pat. No. 6,030,558.

Figure 5:
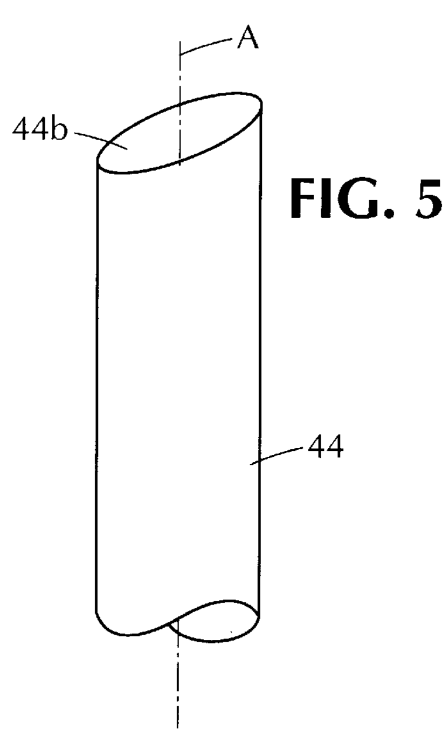
FIGS. 5–8 are fragmentary views showing alternate forms of a liquid delivery portion of the replacement reservoir of FIG. 3.

FIG. 5 shows an alternative configuration for the capillary element 44. In the case of the configuration of FIG. 5, the element 44 is not tapered at the top but instead is cut at a slant relative to its longitudinal axis. This forms an oval shaped upper surface 44*b* as viewed in FIG. 5. The surface 44*b* is inherently larger than the surface 44*a* in the embodiment of FIG. 3; and this makes the capillary element more suitable to larger diameter orifice plates. Conversely, it permits a smaller diameter capillary element for a given diameter orifice plate. It will be noted that the surface 44*b* is not symmetrical about the longitudinal axis of the capillary element 44 as is the surface 44*a* of the embodiment of FIG. 3. Because of this, the capillary element must be properly oriented about its longitudinal axis A in order to be sure that the surface 44*b* will lie flat against the surface of the orifice plate.

Figure 6:
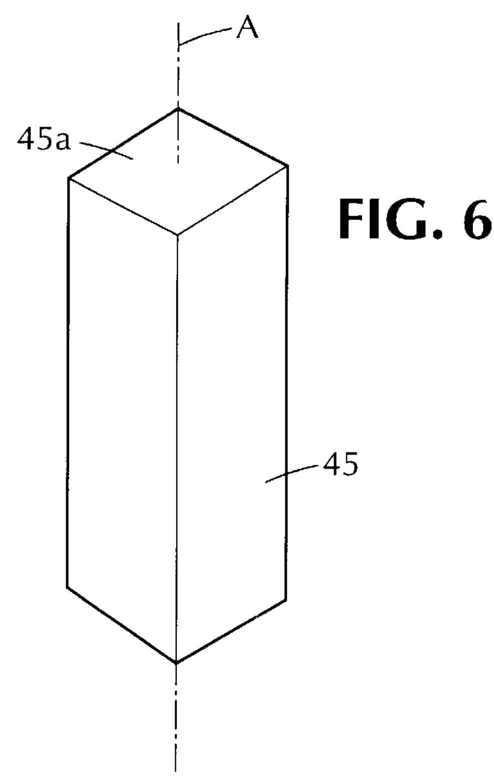
Figure 7:
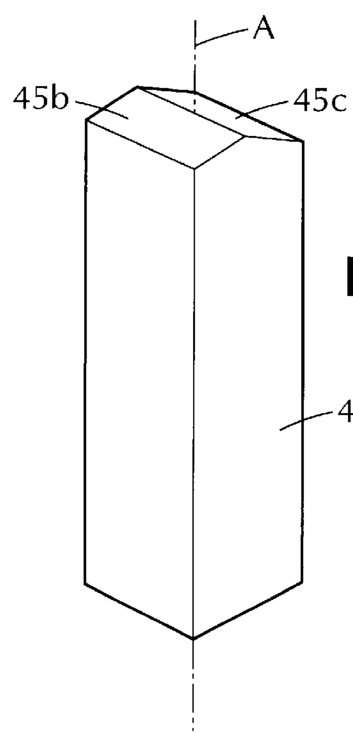
Figure 8:
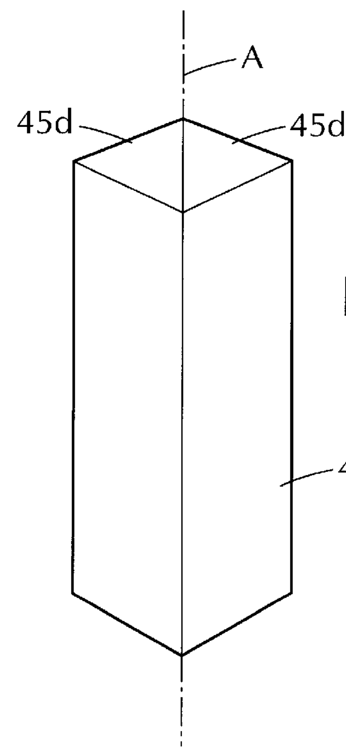

FIG. 6 shows a further alternate capillary element 45. In this embodiment, the capillary element 45 has a rectangular rather than a round cross-section. Otherwise it is of the same construction as the capillary element 44. The rectangular configuration of the element 45, which is shown in FIG. 6 as square, permits many different possibilities for its upper surface 45*a* which abuts the orifice plate of a vibration type atomizer device. Firstly, as shown in FIG. 7, the capillary element 45 may simply be cut from opposed sides to form two opposed slanted surfaces 45*b* and 45*c*. If desired, these surfaces may extend at different angles with respect to the axis A, which will permit the reservoir assembly 40 to be used with different atomizer devices whose orifice plates are tilted at different angles. In another embodiment, shown in FIG. 8 the capillary element 45 may be formed with four flat surfaces 45*d* which extend up from each side to form a pyramid configuration.

The different arrangements described herein, provide different surface areas for the upper surface of the capillary element. A surface area should be chosen such that it corresponds to the surface area of the orifice plate with which the capillary element is to be used. Also, in each of the embodiments, the capillary element 44 or 45 should be oriented about its longitudinal axis A with respect to the liquid container 42 such that when the liquid container is mounted in a vibratory orifice plate type atomizer device, the flat upper surface of the capillary element will be oriented in the same direction as the orifice plate so that it will lie against the orifice plate.

INDUSTRIAL APPLICABILITY

This invention permits a vibrating plate type atomizer to operate effectively to direct a cloud or mist of atomized droplets in a direction other than vertically above the atomizer. Thus, the cloud or mist can be projected from one side of a room in toward the center of the room. The invention additionally provides a novel replacement reservoir having a specially shaped wick which extends vertically up from a liquid container and which is capable of delivering liquid efficiently and effectively to a non-horizontal vibratory atomization plate.

What is claimed is:

1. An atomizer for ejecting small liquid droplets into the atmosphere, said atomizer comprising:

a housing;

a vibratory orifice plate extending in a plane and mounted in said housing with said plane tilted from the horizontal, said orifice plate having a plurality of small orifices formed in a center region thereof;

a vibratory actuator coupled to said plate for causing said orifice plate to vibrate rapidly in a direction perpendicular to its plane; and a replaceable liquid reservoir removably mounted in said housing below said orifice plate, said reservoir comprising a liquid container for containing a supply of liquid to be atomized and a solid, porous and dimensionally stable elongated liquid delivery member extending along a vertical axis from within said liquid container and out through an upper opening of said container, said liquid delivery member having an upper end which is also tilted from the horizontal and which is positioned in said housing such that it extends along a surface of said orifice plate.

2. An atomizer according to claim 1, wherein said liquid delivery member is formed with capillary pores which extend from one end to the opposite end of said member.

3. An atomizer according to claim 1, wherein said upper end of said liquid delivery member has a flat surface.

4. An atomizer according to claim 1, wherein said upper end of said liquid delivery member extends continuously at a fixed angle with respect to said vertical axis.

5. An atomizer according to claim 1, wherein said liquid delivery member has a circular cross-section.

6. An atomizer according to claim 1, wherein said liquid delivery member has a rectangular cross-section.

7. An atomizer according to claim 1, wherein said upper end of said liquid delivery member comprises a pair of flat surfaces which converge at said vertical axis.

8. An atomizer according to claim 6, wherein said upper end of said liquid delivery member comprises flat surfaces in a pyramidal arrangement.

9. A replaceable liquid reservoir for use with a vibrating orifice plate atomizer device, said reservoir comprising:

a liquid container for containing a supply of liquid to be atomized; and an solid, porous and dimensionally stable elongated liquid delivery member extending along a vertical axis from within said liquid container and out through an upper opening of said container, said liquid delivery member having an upper end located at a predetermined position above said container; and said upper end being formed as a surface which intersects said vertical axis and forms an acute angle with said vertical axis.

10. A liquid reservoir according to claim 9, wherein said liquid delivery member is formed with capillary pores which extend from one end to the opposite end of said member.

11. A liquid reservoir according to claim 9, wherein said upper end of said liquid delivery member has a flat surface.

12. A liquid reservoir according to claim 9, wherein said upper end of said liquid delivery member extends continuously at a fixed angle with respect to said vertical axis.

13. A liquid reservoir according to claim 9, wherein said liquid delivery member has a circular cross-section.

14. A liquid reservoir according to claim 9, wherein said liquid delivery member has a rectangular cross-section.

15. A liquid reservoir according to claim 9, wherein said upper end of said liquid delivery member comprises a pair of flat surfaces which converge at said vertical axis.

16. A liquid reservoir according to claim 14, wherein said upper end of said liquid delivery member comprises flat surfaces in a pyramidal arrangement.

* * * * *